United States Patent [19]
Voss

[11] Patent Number: 5,680,432
[45] Date of Patent: Oct. 21, 1997

[54] METHOD AND APPARATUS FOR GENERATING A CIRCULATING X-RAY FOR FAST COMPUTED TOMOGRAPHY

[75] Inventor: Gustav-Adolf Voss, Hamburg, Germany

[73] Assignee: Siemens Aktiengesellschaft, Munich, Germany

[21] Appl. No.: 626,677

[22] Filed: Apr. 2, 1996

[51] Int. Cl.$^6$ ..................................................... H01J 35/30
[52] U.S. Cl. ........................... 378/137; 378/138; 378/121; 378/10
[58] Field of Search .................................... 378/119, 121, 378/137, 138, 10, 12, 13, 21

[56] References Cited

U.S. PATENT DOCUMENTS

| | | | |
|---|---|---|---|
| 5,172,401 | 12/1992 | Asari et al. | 378/137 |
| 5,197,088 | 3/1993 | Vincent et al. | 378/10 |
| 5,504,791 | 4/1996 | Hell et al. | 378/10 |

FOREIGN PATENT DOCUMENTS 2 044 985  3/1979  United Kingdom.

*Primary Examiner*—Don Wong
*Attorney, Agent, or Firm*—Hill, Steadman & Simpson

[57] ABSTRACT

In an apparatus and a method for generating an x-ray beam circulating through a polar angle $\phi$ of $2\pi$ that enables fast computed-tomographic scans is to be generated, an electron beam is generated with a predetermined energy and is injected into a beam guide that guides the electron beam on a spiral path in a plane by means of an axial magnetic field. At a location selectable in the $\phi$-direction, the electron beam is deflected perpendicularly to the plane and onto an essentially annular anode arrangement, so that, proceeding from the point of incidence of the electron beam, x-rays directed onto the center of the anode arrangement are generated. For a scan, the selectable location at which the electron beam is deflected out of the plane is advanced along the spiral path, so that the point of incidence of the electron beam onto the anode arrangement advances correspondingly.

17 Claims, 3 Drawing Sheets

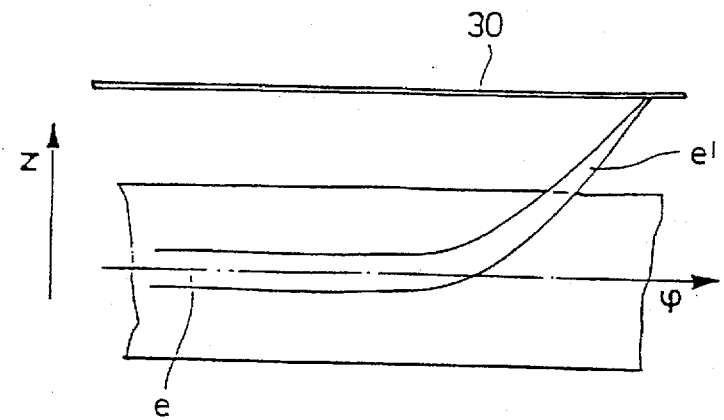
FIG.4a
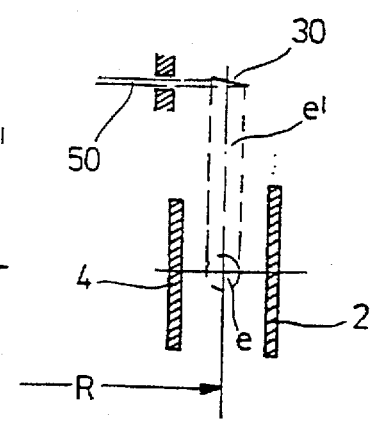
FIG.4b
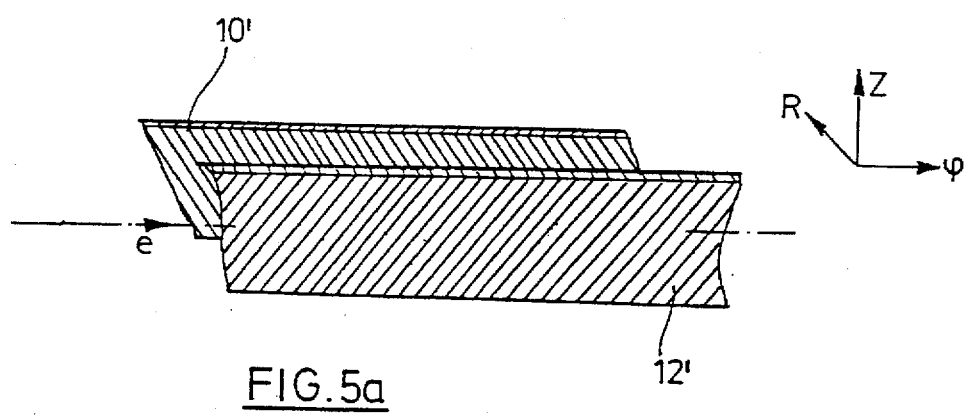
FIG.5a
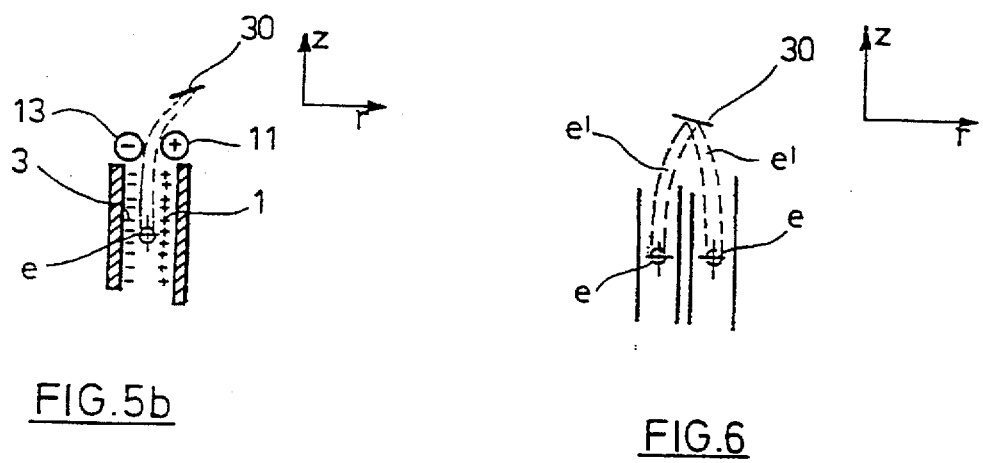
FIG.5b
FIG.6

5,680,432

METHOD AND APPARATUS FOR GENERATING A CIRCULATING X-RAY FOR FAST COMPUTED TOMOGRAPHY

BACKGROUND OF THE INVENTION

1. Field of the Invention

The present invention is directed to an apparatus and method for generating a circulating x-ray beam for fast computed tomography.

2. Description of the Prior Art

Movable x-ray sources and detectors were employed in the original computed tomography apparatus, these having been mounted so as to be rotatable around the examination region in order to successively rotate around the examination region and thus obtain a scanning of successive observation angles in the polar coordinate system angle in the rotation plane. Due to the mechanical adjustments that were needed for only a single revolution, such apparatuses were relatively slow. This was disadvantageous since the data acquisition time for patients for whom a large number of successive tomograms were to be recorded were uncomfortably long.

Further, there is a need for faster scanning times because now images of motion sequences are also sought by means of computed tomographic techniques. This is only possible, however, when the scan times are shorter than the typical time unit of the motion that is to be acquired.

An acceleration of the registration (data acquisition phase) of tomographic images has already been achieved in electron beam tomography. In an electron beam tomography apparatus, a mechanical rotation of radiation sources and detectors is eliminated. A known apparatus of this type has an electron source that generates a horizontally proceeding electron beam with a given energy, and controllable electromagnetic deflection system that successively steers the electron beam onto successive points on a semi-annular anode that is arranged under the examination table. A detector half-ring is arranged lying opposite the anode half-ring. The electron beam is guided over the anode half-ring by the electromagnetic deflection system and successive exposures are thus registered with the detector half-ring over a polar angle range of $\phi$.

SUMMARY OF THE INVENTION

An object of the present invention is to provide a method and an apparatus for generating an x-ray for fast scanning over a polar angle range of $2\pi$ for computed tomography.

According to the inventive method, an electron beam having a given energy is generated, and is guided on a spiral path in a plane by a beam guidance system with an axial magnetic field and thereby being able to cover at least a polar angle of $2\pi$. A radial magnetic field proceeding in the plane of the spiral path is generated along the spiral beam guidance system, this magnetic field deflecting the electron beam traveling in the beam guidance system perpendicularly from the plane and focusing it in the $\phi$-direction onto a substantially annular anode arrangement that is concentric with the spiral path. X-rays are generated at the location of incidence of the electron beam on the anode, whereby diaphragms select a ray beam directed onto the center of the essentially annular anode arrangement. Subsequently, the location at which the radial magnetic field is generated is shifted along the spiral path, so that the location at which the electron beam is deflected out of the spiral path and the location at which the deflected electron beam strikes the anode arrangement are correspondingly varied. As a result of circulating scanning of the deflection location, i.e. by circulating scanning of the location of the radial magnetic field along the spiral path, the point of incidence of the deflected electron beam migrates in correspondingly scanning fashion through the polar angle $\phi$ in the essentially annular anode arrangement. As a result, the point of incidence of the electron beam migrates around the essentially annular anode arrangement, and the selected ray beam, directed into the center, thus correspondingly travels circularly through the polar angle of the anode arrangement.

The inventive apparatus have a beam guidance channel that proceeds spirally in a plane through a polar angle $\phi$ of at least $2\pi$. Means for generating guide fields generate an axial magnetic field proceeding perpendicularly to the plane in the beam guidance channel. The strength of the axial magnetic field increases along the spiral beam guidance channel such that an electron beam having a prescribed energy along the spiral path is guided essentially centrally in the beam guidance channel. Further, ejection field (kick-out field) generating means are provided with which a radial magnetic field proceeding essentially in the spiral plane can be generated in a region of the beam guidance channel at a selectable $\phi$-position. An electron beam traveling in the beam guidance channel is thereby deflected out of the plane and is focussed in $\phi$-direction onto an essentially annular anode arrangement concentric with the beam guidance channel. X-rays are generated at the point of incidence of the electron beam on the anode. The ejection field generating means are controlled by control means such that the $\phi$-position of the predetermined region in which the radial magnetic field is generated is shifted along the spiral path in scanning fashion. Corresponding to the deflection of the electron beam shifted along the spiral path, the point of incidence of the deflected electron beam onto the essentially annular anode arrangement also shifts, so that the point of origin of the x-radiation is shifted in circulating fashion around the essentially annular anode arrangement, so that the selected ray beam irradiates the center of the anode arrangement successively from all directions.

The inventive method and the inventive apparatus enable extremely fast scanning with an x-ray over a polar angle of $2\phi$, with no mechanical displacement being used.

In an embodiment, the guide field generating means include two spirally arranged metal plates that enclose the beam guidance channel between them, and conductor windings would in the $\phi$-direction at the metal sheets. The conductor windings arranged at the inner, spiral metal sheet and those arranged at the outer metal sheet can be supplied with oppositely flowing electrical currents in order to thus generate an axial magnetic field between the metal sheets in the beam guidance channel.

In another embodiment, the strength of the magnetic field along the spiral path increases from the outside toward the inside by virtue of the height of the metal sheets decreasing from outside to inside along a revolution of the spiral, so that the axial magnetic field increases from outside to inside given constant currents in the conductor windings.

In a further embodiment, the conductor windings are designed such that a higher current density is present at the inner metal sheet than at the outer metal sheet, as a result of which the axial magnetic field decreases from inside to outside in radial direction. This radial field gradient effects a focusing of the circulating electron beam according to the principle of weak focusing.

In an alternative embodiment, spreading of the electron beam is opposed with a solenoid coil that is arranged following the spiral shape of the beam guidance channel and extending into the beam channel in order to generate a magnetic field in the $\phi$-direction. The solenoid coil projects beyond the beam guidance channel and also surrounds the anode arrangement. This means that the deflected electron beam need not penetrate the solenoid coil in order to reach the anode arrangement, which would result in a considerable disturbance of the beam and an ungovernable heating of the solenoid coil. Instead, the deflected electron beam reaches the anode undisturbed, and the x-ray generated at the point of incidence at the anode need not penetrate the solenoid coil in order to be incident onto the center of the anode arrangement. This arrangement is preferred since the x-rays contain only a fraction of the energy of the electron beam and because of the smaller effective cross-section of x-rays in the material of the solenoid coil.

There are fundamentally two alternative embodiments for the anode arrangement. The anode arrangement can coincide with the spiral shape of the beam guidance channel and be arranged thereabove and concentric thereto. In this case, the anode arrangement forms a strip-shaped metal surface that is spirally arranged like the beam guidance channel, but above it. In this case, the electron beam must be deflected upwardly in order to strike the metal strip of the anode arrangement. The essentially annular anode is not closed in this case but has a discontinuity at one point of its circumference. In an alternative embodiment, the anode arrangement can be fashioned as a closed circular ring, whereby correction fields are then necessary in order to cause the electron beam, deflected from the spiral beam guidance channel from a specific location, to strike the annular anode surface. This can be effected, for example, by correction fields that are generated between the beam guidance channel and the anode arrangement.

In any case, the strip-shaped metal surface of the anode arrangement is preferably slightly inclined relative to the plane of the essentially annular anode arrangement, so that the metal surface—as seen from the center of the anode arrangement—has a very small effective expanse perpendicular to the plane of the anode arrangement. A very small size of the x-ray origination in this expanse is thereby achieved. A beam directed onto the center of the anode arrangement is selected by diaphragms, but this beam is inclined slightly relative to the plane of the anode arrangement so that it reaches a detector ring arranged adjacent to the anode ring.

The ejection fields for deflecting the electron beam are preferably generated by a number of conductor windings arranged at both sides of the beam guidance channel over the entire length thereof. For example, these can be wound around the metal sheets, so that the surface normal of each turn proceeds essentially in the direction of electron beam travel. The conductor windings can be individually and selectively supplied with current, for example by connecting a transistor to each conductor winding. One or more neighboring conductor windings are supplied with current at one side of the beam guidance channel, whereas the corresponding conductor windings lying opposite at the other side of the beam guidance channel are supplied with a current having the opposite direction; as a result, a radial magnetic field is generated in the beam guidance channel. When a number of successive conductor windings in the $\phi$-direction are supplied with current, the radial magnetic field increases linearly in the region of these conductor windings. The $\phi$-position of the radial magnetic field is shifted along the spiral path by control means by advancing the feed and tap points at the conductor windings, so that the radial magnetic field circulates along the spiral path and rotates corresponding to the point at which the electron beam is deflected from the spiral plane.

DESCRIPTION OF THE DRAWINGS

FIG. 4a is a schematic, lateral view within the beam guidance channel in the apparatus of the invention.

FIG. 4b is a cross section in the R-Z plane of the beam guidance channel from FIG. 4a.

FIG. 5a is a perspective view of a modified embodiment of the beam guidance channel in the apparatus of the invention.

FIG. 5b is a cross sectional view of an alternative embodiment of beam guidance channel and anode arrangement in the apparatus of the invention.

FIG. 6 is a cross sectional view of the beam guidance channel in the region where start and end region of the spiral beam guidance channel overlap in the apparatus of the invention.

DESCRIPTION OF THE PREFERRED EMBODIMENTS

Figure 1:
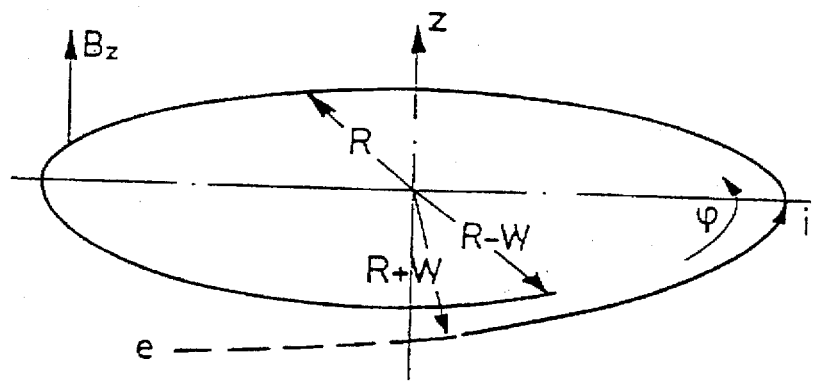
FIG. 1 is a schematic illustration of the path of an electron beam in the beam guidance channel in the apparatus of the invention.

FIG. 1 shows a schematic illustration of the spiral path on which an electron beam e is guided through the beam guidance channel. At the point of entering into the beam guidance channel, the initial radius of the spiral path amounts to R+W, which decreases along the path after one revolution to R-W. Typical values for R are 0.5-1 m and 2.5 cm for W. The energy of the electrons can, for example, be 140 KeV, and the current intensity of the beam can be 1 A. The electron beam e is guided on the illustrated spiral path by the axial magnetic field B effective in the beam guidance channel.

Figure 2:
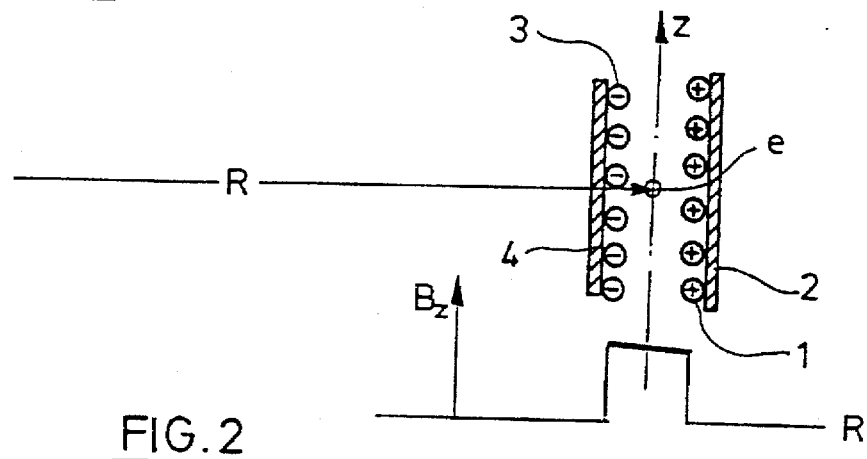
FIG. 2 is a schematic sectional view of the beam guidance channel in the apparatus of the invention.

The beam guidance channel is enclosed by iron plates 2 and 4 following the spiral path at both sides, the axial magnetic field B is generated in the beam guidance channel by conductor windings 1 and 3 wound in the $\phi$-direction. The conductor windings 1 or 3 respectively circulating at the inside of the iron plates 2 and 4 are supplied with oppositely directed currents, so that an axial magnetic field B, whose curve is schematically shown at the bottom of FIG. 2, is generated between the iron plates 2 and 4. As a result of different current occupation densities at the inwardly disposed iron plate 4 and the outwardly disposed iron plate 2, the magnetic field generated is not constant but, as indicated in FIG. 2, decreases in the radial direction. This field gradient opposes spreading of the electron beam e based on the principle of weak focusing. The aforementioned different current densities on the inside and outside plate can be generated, for example, by virtue of the outer iron plate 2, as in the illustration of FIG. 2, having a larger height, so that a lower current density results given the same number of conductor turns.

In order to guide the electron beam e on the spiral path, the axial guide field B must increase along the spiral path.

This can be effected, for example, by gradually reducing the height of the metal plates 2 and 4 along the spiral path, so that a corresponding increase in the current density and a corresponding increase of the axial guide field B result.

Figure 3:
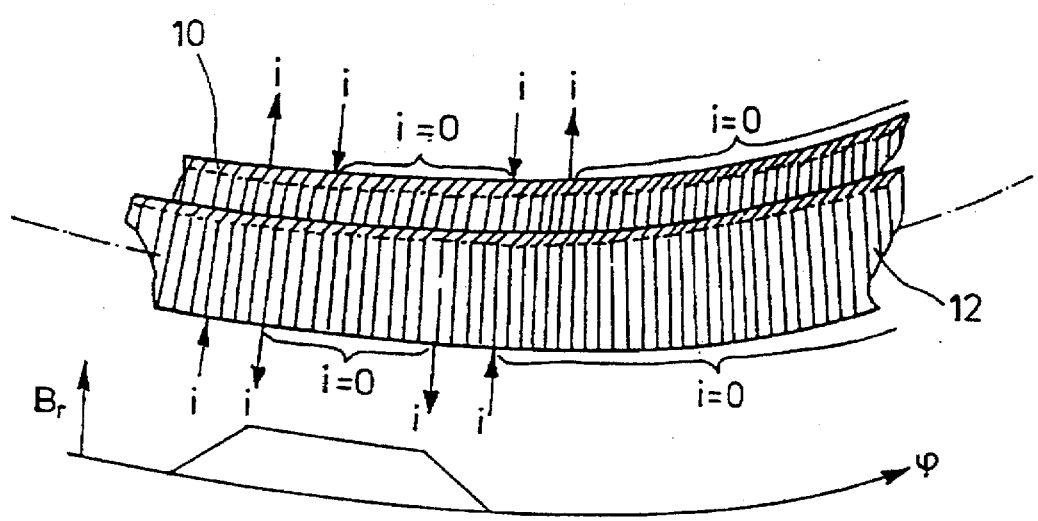
FIG. 3 is a perspective view of a part of the beam guidance channel in the apparatus of the invention.

In order to be able to deflect the electron beam e upwardly out of the spiral plane at an arbitrary location φ, ejection field generating means that are schematically shown in FIG. 3, are present. What is shown is a portion of the beam guidance channel, and the iron plates 2 and 4 at both sides of the beam guidance channel are provided with current windings 10 and 12. The planes of the current windings 10 and 12 reside essentially perpendicularly on the spiral plane. The current windings 10 an d 12 can be locally driven, so that an extremely small region of current windings 10 and 12 in the φ-direction, (an individual current winding in the extreme case) can be selectively supplied with current. In the illustrated example, a current I or −I is supplied to the current windings 10 and 12 at a specific φ-position, and an opposite current −I or I is supplied a few current turns further in the φ-direction, so that a current flows only over these enclosed current windings and does not flow beyond in the other current windings. These oppositely disposed current windings 10 and 12 with opposite current flows generate a magnetic field $B_r$ that proceeds essentially in radial direction relative to the spiral plane and whose amplitude curve is shown schematically at the bottom of FIG. 3. The radial magnetic field $B_r$ increases linearly in the region of the current windings supplied with current. In order to avoid a larger magnetic flux in the iron plates in the φ-direction, it is preferred that a radial magnetic field $B_r$ with opposite polarity is generated at a remote location on the circumference, this being generated in FIG. 3 by an opposite current feed at a remote position at the circumference.

The functioning of the ejection field generating means as shown in FIG. 3 is illustrated in FIG. 4a. The electron beam e is deflected out of the spiral plane over an extremely short distance in the Z-direction at the location of the radial field $B_r$. In order to achieve such a deflection, the amplitude of the radial magnetic field is typically significantly larger than that of the axial magnetic field; for example, the axial magnetic field $B_z$ may be 30 G, whereas the radial ejection field $B_r$ may be 110 G. At the exit from the $B_r$ field, the beam e' is focused in the φ-direction (edge focusing) and is steered onto the anode. The metal surface of the anode arrangement 30 onto which the electron beam e' is steered is inclined slightly relative to the plane of the anode, so that the metal surface 30—as seen from the center of the essentially annular anode arrangement—has an extremely small Z-expanse. In this way, the size of the x-ray origination is extremely well-defined by the slight expanse in Z-direction, and by good focusing of the electron beam e' in the φ-direction.

The point of the deflection of the electron beam e in the φ-direction is varied by shifting the region of current windings to which current is supplied as shown in FIG. 3 along the spiral path. The point of incidence of the deflected electron beams e' on the metal surface of the anode varies correspondingly and the point of origination of the x-radiation in the φ-direction also correspondingly varies. The turn spacing of the current windings 10 and 12 can amount to less than 1 mm, so that the focal spot on the anode can be shifted with a corresponding precision in the φ-direction. For local current supply of the current windings 10 and 12, each current winding 10 and 12 must be provided with a controllable means for feeding current; this can be accomplished, for example, by transistors.

There are two fundamental possibilities for shaping the anode arrangement. The strip-shaped metal surface of the anode 30 can follow the spiral shape of the beam guidance channel. The strip-shaped metal surface 30 then has a spiral shape and has a circumferential gap of a width 2 W; this, however, amounts to less than 10% of the radius given typical dimensions.

In an alternative embodiment, an anode 30 having an annular metal surface is employed. In order to assure that the deflected electron beam e' strikes the anode ring, for every deflection location of the electron beam e along the spiral electron path, a φ-dependent, radial beam deflection is necessary. This can be achieved, for example, by correction fields that can be provided by specifically shaped current windings 11 and 13 along the spiral path, as shown in FIG. 5b. Alternatively, the inclination of the current windings 10 and 12 shown in FIG. 3 can be varied φ-dependent in order to achieve the necessary correction, as shown in FIG. 5a. The result of such corrections is schematically shown in FIG. 6, in which the beam guidance channel is shown in cross section in the overlap region of start and end region, whereby the start region of the beam guidance channel lies at a radius R+W and the end region lies at a radius R−W, and the annular anode has a radius of R. The correction field generating means 101 and 121 or 11 and 13 ensure that the deflected electron beam e' is incident onto the anode ring in any case.

For a non-relativistic particle beam, axially and radially defocusing space charge effects arise given a high beam current. These increase as the beam cross-section decreases. The weak focusing set forth herein compensates the space charge effects given a beam current of 1 A, a beam energy of 140 KeV and a circular beam cross-section having a radius of 1 cm. Given lower energy or smaller beam cross-section, the current would have to be reduced.

The above-described space charge effects occur in full strength only given a perfect vacuum or artificial ion extraction. In the apparatus disclosed herein, there will be no significant ion effects because of the electrical space charge fields of the beam together with the magnetic guide field. If this should nonetheless be the case, an ion accumulation could be easily avoided by additional, radial electrical fields.

Due to the space charge effects of the rotating electron beam and the weak focusing with limited effect, the above-described apparatus is current-limited, as indicated above.

Figure 7:
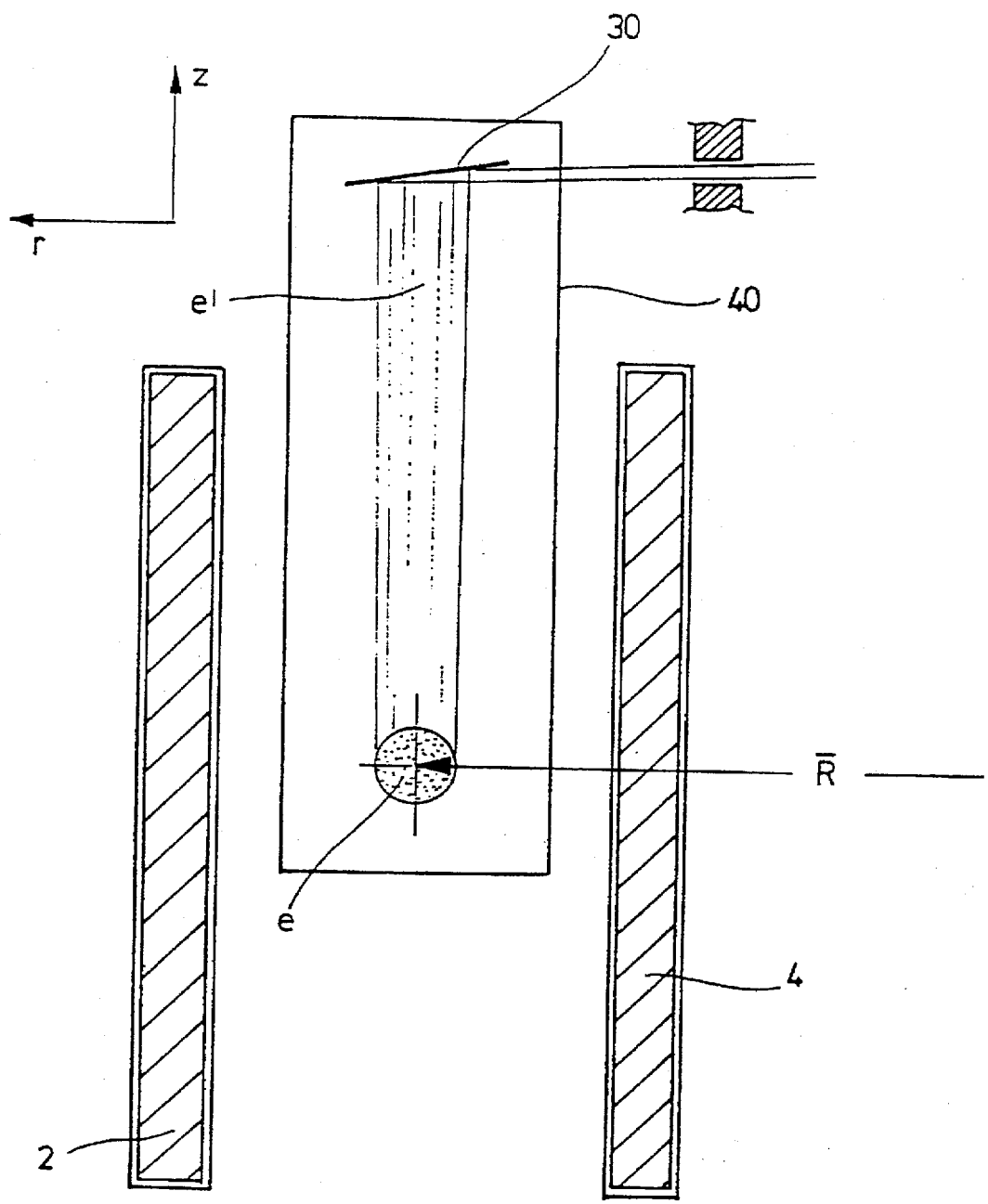
FIG. 7 is a sectional view of an embodiment wherein the electron beam is focused by a longitudinal solenoid field.

This limitation is largely eliminated when a longitudinal solenoid field is employed for the beam focusing of the electron beam instead of a weak gradient field (see FIG. 2). An embodiment of the inventive apparatus wherein the electron beam e is focused by a longitudinal solenoid field is shown in FIG. 7. A solenoid 40 following the spiral path is arranged between the iron plates 2 and 4, of the beam guidance channel, both the electron beam e as well as the anode being arranged in the cross-section of the solenoid 40. The anode likewise lies inside the solenoid 40, so that the problem of extracting the electron beam e' through the turns of the solenoid is eliminated. Instead, the x-radiation generated on the metallic surface of the anode only has to pass extremely thin wires of the solenoid 40, this leading to an acceptable thermal load on the wires.

Given the embodiment provided in FIG. 7, the ejection field can be generated in turn as shown in FIG. 3, FIG. 4a and FIG. 4. On the other hand, a constant magnetic field can be employed instead of the radially variable guide field $B_r$ shown in FIG. 2 since the weak focusing is no longer required.

An important idea of the present application is, given an apparatus for generating a circulating x-ray beam for fast computer tomography, to provide a solenoid coil 40 that extends into the beam guidance channel, that follows the beam guidance channel in φ-direction in order to focus an electron beam e' in the inside of the solenoid coil 40 in the beam guidance channel, whereby the anode arrangement 30 lies inside the solenoid coil 40.

Instead of a spiral beam guidance channel, the apparatus can have a circular or approximately circular beam guidance channel.

Although modifications and changes may be suggested by those skilled in the art, it is the intention of the inventor to embody within the patent warranted hereon all changes and modifications as reasonably and properly come within the scope of his contribution to the art.

I claim as my invention:

1. An apparatus for generating a circulating x-ray beam for fast computed tomography, comprising:

a beam guidance channel proceeding in a spiral in a plane through a polar angle φ of at least 2π;

means for introducing an electron beam having a prescribed energy into said beam guidance channel;

means for generating an axial magnetic field effective in said beam guidance channel and directed perpendicularly to the plane of said beam guidance channel, and having a strength which increases along the spiral of the beam guidance channel for guiding said electron beam having said prescribed energy substantially centrally in said beam guidance channel;

ejection field generating means for generating a radial magnetic field proceeding substantially in the plane of said beam guidance channel in a region of said beam guidance channel at a selectable φ-position, for deflecting the electron beam traveling in said beam guidance channel out of said plane of said beam guidance channel and focussed in a φ-direction;

a substantially annular anode disposed concentrically relative to said beam guidance channel and unto which said electron beam, when deflected out of said plane of said beam guidance channel focussed in said φ-direction, is incident for producing x-rays; and control means for controlling said ejection field generating means for circulating said region, at which said electron beam is deflected, along said beam guidance channel in the φ-direction.

2. An apparatus as claimed in claim 1 wherein said means for generating said axial magnetic field comprise:

two metal plates spirally arranged in the φ-direction and disposed perpendicularly relative to said plane of said beam guidance channel, said beam guidance channel being disposed between said two metal plates and one of said metal plates comprising an inner plate and the other of said metal plates comprising an outer plate;

conductor windings respectively wound on said inner and outer plates and proceeding in the φ-direction; and means for supplying respective currents to the conductor windings on said inner and outer plates in respectively opposite current directions for generating said axial magnetic field in said beam guidance channel.

3. An apparatus as claimed in claim 2 wherein each of said metal plates has a height which decreases along said spiral in a direction of travel of said electron beam in said beam guidance channel for increasing said strength of said axial magnetic field along said direction or travel with respective, constant currents in said conductor windings.

4. An apparatus as claimed in claim 2 wherein said conductor windings are respectively wound on said inner and outer plates for producing a higher current density at said inner plate than at said outer plate, for causing said axial magnetic field to decrease from inside to outside in a radial direction of said beam guidance channel.

5. An apparatus as claimed in claim 1, comprising:

a solenoid coil extending into said beam guidance channel and spirally following said beam guidance channel in the φ-direction for focussing said electron beam in an inside of said solenoid coil in said beam guidance channel, and said anode being disposed inside said solenoid coil.

6. An apparatus as claimed in claim 1 wherein said anode comprises a strip-shaped metal surface following the spiral of said beam guidance channel, and disposed concentrically above said beam guidance channel.

7. An apparatus as claimed in claim 6 wherein said surface of said anode is inclined relative to a center of said anode so that said surface is visible from said center of said anode.

8. An apparatus as claimed in claim 1 wherein said anode comprises an annular metal surface having a diameter substantially equal to an average diameter of said spiral beam guidance channel, and disposed concentrically above said beam guidance channel, and said apparatus further comprising correction field generating means for directing the electron beam which was axially deflected out of said beam guidance channel onto said annular metal surface of said anode.

9. An apparatus as claimed in claim 8 wherein said surface of said anode is inclined relative to a center of said anode so that said surface is visible from said center of said anode.

10. An apparatus as claimed in claim 8 wherein said ejection field generating means comprise a plurality of conductor windings disposed at opposite sides of said beam guidance channel along an entire length of said beam guidance channel, each conductor winding in said plurality of conductor windings having a surface normal inclined relative to the plane of said beam guidance channel for simultaneously serving as said correction field generating means, and means for selectively supplying said conductor windings in said plurality of conductor windings in the φ-direction with current.

11. An apparatus as claimed in claim 1 wherein said ejection field generating means comprise a plurality of conductor windings disposed at opposite sides of said beam guidance channel along an entire length of said beam guidance channel, each conductor winding in said plurality of conductor windings having a surface normal substantially in said φ-direction, and means for selectively supplying conductor windings in said plurality of conductor windings in the φ-direction with current.

12. An apparatus as claimed in claim 11 wherein said guide field generating means include an inner metal plate and an outer metal plate respectively having guide field generating conductor windings thereon, and wherein said plurality of conductor windings of said ejection field generating means are wound on said inner and outer metal plates.

13. An apparatus as claimed in claim 11 wherein said means for selectively supplying said-conductor windings in the φ-direction with current include a plurality of transistors, respectively connected to said conductor windings of said plurality of conductor windings, and each transistor being switchable for conducting current to the conductor winding connected thereto, and said means for selectively supplying said conductor windings with current comprising means for successively, respectively switching said transistors in the φ-direction to become conductive.

14. A method for generating an x-ray beam for computed tomography comprising the steps of:
- generating an electron beam having a predetermined energy;
- introducing said electron beam into a beam guide channel proceeding through a polar angle of $2\pi$;
- introducing said electron beam into said beam guide channel and guiding said electron beam along a planar, spiral path in said beam guide channel by interacting said electron beam with an axially-directed magnetic field;
- deflecting said electron beam out of said plane at a selectable location onto a substantially annular anode disposed above said beam guide channel;
- producing x-rays directed toward a center of said substantially annular anode by striking said anode with said electron beam; and
- varying said selectable location at which said electron beam is deflected from said plane along said spiral so that a location on said annular anode which is struck by said electron beam correspondingly varies along said annular anode.

15. An apparatus for generating a circulating x-ray beam for fast computed tomography comprising:
- a beam guidance channel proceeding through a polar angle of at least $2\pi$;
- means for introducing an electron spiral beam having a predetermined energy into said beam guidance channel;
- guide field generating means for generating a magnetic field effective in said beam guidance channel for guiding said electron beam having said predetermined energy substantially centrally in said beam guidance channel;
- a solenoid coil extending into said beam guidance channel and following said beam guidance channel; and
- an anode disposed inside said solenoid coil for producing x-rays when struck by said electron beam.

16. An apparatus as claimed in claim 15 wherein said beam guidance channel is contained in a single plane.

17. An apparatus as claimed in claim 15 wherein said beam guidance channel is substantially annular.

* * * * *